US008626764B2

(12) United States Patent
Erlanger et al.

(10) Patent No.: US 8,626,764 B2
(45) Date of Patent: Jan. 7, 2014

(54) METHODS, SYSTEMS AND COMPUTER PROGRAM PRODUCTS FOR ORGANIZING AND/OR MANIPULATING COHORT BASED INFORMATION

(75) Inventors: Linda Susan Erlanger, Branford, CT (US); Michael Harold Eubank, Minneapolis, MN (US); Robert R. Friedlander, Southbury, CT (US); James R. Kraemer, Santa Fe, NM (US); Meredith Keating Moore, Washington, DC (US)

(73) Assignee: International Business Machines Corporation, Armonk, NY (US)

( * ) Notice: Subject to any disclaimer, the term of this patent is extended or adjusted under 35 U.S.C. 154(b) by 2321 days.

(21) Appl. No.: 11/404,330

(22) Filed: Apr. 13, 2006

(65) Prior Publication Data
US 2007/0244701 A1 Oct. 18, 2007

(51) Int. Cl.
*G06F 7/00* (2006.01)
*G06F 17/30* (2006.01)
(52) U.S. Cl.
USPC ............................ 707/737; 707/738; 707/740

(58) Field of Classification Search
USPC .......................................... 707/737, 738, 740
See application file for complete search history.

(56) References Cited

U.S. PATENT DOCUMENTS

| 6,278,999 B1 * | 8/2001 | Knapp ............................. 707/9 |
| 2002/0049772 A1 * | 4/2002 | Rienhoff et al. ........... 707/104.1 |
| 2004/0215981 A1 * | 10/2004 | Ricciardi et al. ............. 713/202 |

\* cited by examiner

*Primary Examiner* — Mariela Reyes
(74) *Attorney, Agent, or Firm* — Yudell Isidore Ng Russell PLLC

(57) ABSTRACT

Methods, systems and computer program products are provided for storing, organizing and/or manipulating cohort based information associated with a research study. Project information associated with a first project is received at an interface of a computer database environment. The project information associated with the first project includes cohort information associated with one or more cohorts of the first project and patient information associated with members of the one or more cohorts of the first project. A first virtual project drawer is generated associated with the first project to be stored in the computer database environment. The first virtual project drawer includes the project information associated with the first project, at least one cohort file and/or at least two cohort member files.

45 Claims, 4 Drawing Sheets

United States Patent US 8,626,764 B2

METHODS, SYSTEMS AND COMPUTER PROGRAM PRODUCTS FOR ORGANIZING AND/OR MANIPULATING COHORT BASED INFORMATION

FIELD OF THE INVENTION

The invention relates to data processing in general and, more particularly, to organization of data.

BACKGROUND OF THE INVENTION

Research in many industries, for example, the healthcare industry, may be done at a cohort level. A cohort is simply a set or group of things or people sharing similar characteristics. The "characteristics" of the cohort can be chosen by the administrator/owner of the study such that the characteristics lend themselves to the research study in a meaningful way. For example, if a researcher were studying the effectiveness of a drug on breast cancer patients, the list of characteristics may include female, between the ages of 35 and 50 and stage 3 breast cancer.

Research studies can last for long periods of time, especially in the healthcare industry where diseases and conditions may progress very slowly and drugs used thereon may only have an effect over time. Keeping track of the all the information, for example, lab/test results, MRIs, x-rays, symptoms before and after administering a drug, side effects and the like, throughout the study may be difficult and time consuming. Furthermore, even if the information is recorded effectively, finding and/or searching the information in the future may also be difficult.

SUMMARY OF THE INVENTION

Some embodiments of the present invention provide methods, systems and computer program products for storing, organizing and/or manipulating cohort based information associated with a research study. Project information associated with a first project is received at an interface of a computer database environment. The project information associated with the first project includes cohort information associated with one or more cohorts of the first project and patient information associated with members of the one or more cohorts of the first project. A first virtual project drawer is generated associated with the first project to be stored in the computer database environment. The first virtual project drawer includes the project information associated with the first project, at least one cohort file and/or two or more cohort member files.

In further embodiments of the present invention, project information associated with a second project may be received at the interface of the computer database environment. The project information associated with the second project may include cohort information associated with at least one cohort of the second project and patient information associated with members of the at least one cohort of the second project. A second virtual project drawer associated with the second project to be stored in the computer database environment may be generated. The second project drawer may include the project information associated with the second project, one or more cohort files and/or two or more cohort member files.

In still further embodiments of the present invention, a query may be generated so as to locate project information, cohort information and/or patient information associated with the first and/or second projects. The first and/or second project drawers may be searched according to the generated query so as to locate results therein that may be relevant to the research study. A report may be generated including the located results.

In some embodiments of the present invention, a query may be generated so as to locate at least one member and/or possible member of a statistically balanced control cohort. The query may be generated using the following equations:

to minimize a sum of weights for a set of a control pairing, the following equation is used:

$$\sum_{i=1}^{n}\sum_{j=1}^{m} \text{Weight}_{i,j} * SOS_{i,j},$$

where n is a patient number in a treatment cohort and m is a patient number in the statistically balanced control cohort, subject to $$\sum_{i=1}^{n} SOS_{i,j} = 1 \text{ For } j = 1, m.$$

Each member of the treatment cohort may be matched to exactly one member of the statistically balanced control cohort represented by the following equation:

$$\sum_{j=1}^{m} SOS_{i,j} \leq 1 = 1 \text{ For } i = 1, n.$$

Members of the statistically balanced control cohort can be used zero or one times represented by the following equation:

$$SOS_{i,j} \epsilon 0,1.$$

In further embodiments of the present invention, the generated query may be modified. The first and/or second project drawers may be searched according to the modified query so as to locate modified results therein that may be relevant to the research study. A modified report may generated including the modified results. The generated reporting may be modified and/or customized.

In still further embodiments of the present invention, a cohort file may be built based on the generated report. The generated report may be saved. The generated report may be scheduled for a run. A delivery method may be determined for the generated report. A user may drill down into the generated report to reveal underlying detail associated with the located results.

In some embodiments of the present invention, the cohort of the first project and/or the cohort of the second project may belong to both the first and second projects. In certain embodiments of the present invention, existing cohort files and/or member files may be split, copied and/or merged to provide the cohort file and/or member files associated with the first project.

In further embodiments of the present invention, the project information associated with the first project may further include owner information, authorized user information, a title of the first project and/or dates associated with the first project.

In still further embodiments of the present invention, the cohort members of the first project may share one or more characteristics that define the cohort associated with the first project. Each of the cohort members of the first project may have one or more roles associated therewith. The one or more roles may include initial data capture, control, rejected, drug, treatment and/or dropped.

In some embodiments of the present invention, the first virtual project drawer may include multiple cohort files that each include at least two cohort member files. In certain embodiments of the present invention, a current user may be authorized at the interface of the computer database environment so as to reduce the possibility of access by unauthorized users. The research study may be associated with a healthcare issue.

DETAILED DESCRIPTION OF EMBODIMENTS OF THE INVENTION

Figure 1:
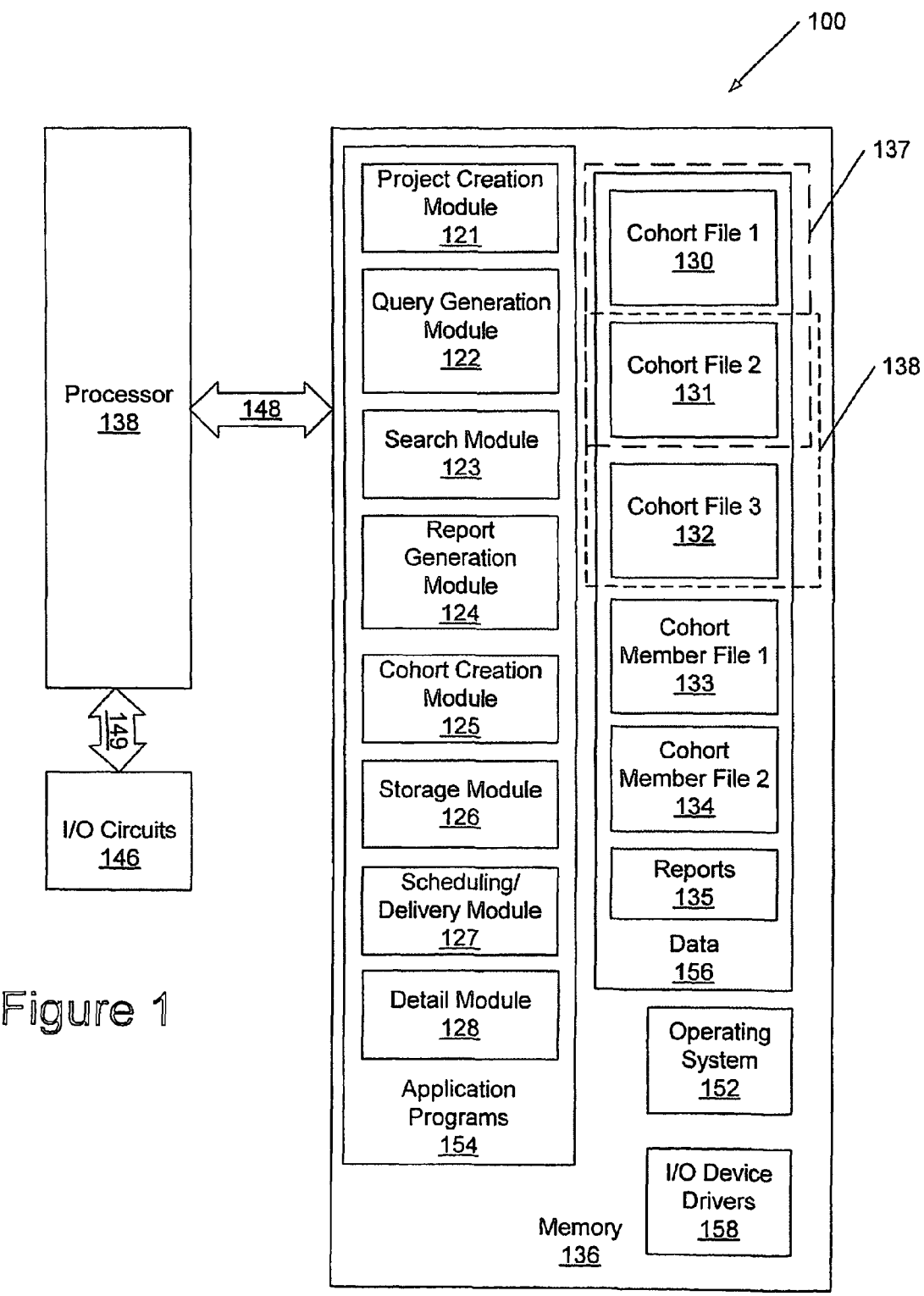
FIG. 1 is a block diagram illustrating systems according to some embodiments of the invention.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another element. Thus, a first element discussed below could be termed a second element without departing from the teachings of the present invention.

As will be appreciated by one of skill in the art, the invention may be embodied as a method, data processing system, or computer program product. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language or in a visually oriented programming environment, such as VisualBasic.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The invention is described in part below with reference to a flowchart illustration and/or block diagrams of methods, systems and computer program products according to embodiments of the invention. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Research in many fields, for example, healthcare, may be conducted using cohort data. As used herein, "cohort" refers to a set or group of things or people sharing similar characteristics. Characteristics may include, for example, physical characteristics, presence or absence of a condition or conditions, age, geographic location and the like. The cohort may be defined by the person conducting the research study and a research study may include one or more cohorts. For example, a researcher may be researching the effect of a particular drug on breast cancer patients. Thus, the cohort may be defined by characteristics including female, breast cancer, from 25-35 years of age and with BRCA1 or BRCA2 cancer-predisposing mutations.

It will be understood that although research studies are discussed herein with respect to the healthcare field, embodiments of the present invention are not limited to this field. For example, embodiments of the present invention may be used for studies in any field that lend themselves to the use of cohorts without departing from the scope of the present invention.

Currently, there is no easy and convenient way of maintaining complete records of the global differences between treatment and control cohorts of research studies involving multiple cohorts. Typically, at the end of a research study (project), the owner (administrator) of the study will publish the study (or report associated therewith). The information published can be very detailed and without a method or system for maintaining the information, it could be very difficult to consolidate the information and present it in a useful way. Furthermore, since there is no easy way to maintain information associated with the study, not everything may be recorded. For example, each time a potential patient for the study is considered and denied, the information associated with this candidate and why he or she was rejected may not be recorded. Thus, the study owner may be accused of "cherry picking" the members of the study and have nothing documented to prove otherwise.

Many times when a research study is performed, two cohorts may be used in the study. The two cohorts may be a initial cohort and a cohort that is statistically balanced to the initial cohort. In other words, the initial study may include a 100 member cohort and a statistically balanced cohort having 100 members, each of which has demographic, genetic, and life style factors as close as possible to a corresponding member of the initial cohort. Without any method or system of recording the data with respect to the initial cohort and its 100 members, choosing the members of the statistically balanced cohort may be relatively difficult.

Thus, according to some embodiments of the present invention methods, systems and computer program products for storing, organizing and/or manipulating cohort based information associated with a research study are provided. According to some embodiments of the present invention, a study owner (administrator) may create a virtual file drawer that includes information on one or more cohorts for the study and the members of these cohorts. Furthermore, the owner may store any information associated with the study in the virtual file drawer associated with the study. The information in the virtual file drawer may be saved in such a way that it can be searched, manipulated and the like. Methods, systems and computer program products according to some embodiments of the present invention may also allow research queries, for example, queries that were used to generate the cohort, to be stored and the stored research queries to be run over time. The methods, systems and computer program products according to some embodiments of the present invention may be configured to recall details of the previously run queries, for example, which members were excluded due to death. This may be useful in a research study extending over multiple years. Details of some embodiments of the present invention will be further discussed below with respect to FIGS. 1 through 5.

Embodiments of the present invention will now be discussed with respect to FIGS. 1 through 5. FIG. 1 illustrates an exemplary data processing system 100 or computer database environment that may be included in devices operating in accordance with some embodiments of the present invention. As illustrated, the data processing system 100 includes a processor 138, a memory 136 and input/output circuits 146. The data processing system 100 may be incorporated in, for example, a personal computer, server, router or the like. The processor 138 communicates with the memory 136 via an address/data bus 148 and communicates with the input/output circuits 146 via an address/data bus 149. The input/output circuits 146 can be used to transfer information between the memory 136 and another computer system or a network using, for example, an Internet protocol (IP) connection. These components may be conventional components such as those used in many conventional data processing systems, which may be configured to operate as described herein.

In particular, the processor 138 can be any commercially available or custom microprocessor, microcontroller, digital signal processor or the like. The memory 136 may include any memory devices containing the software and data used to implement the functionality circuits or modules used in accordance with embodiments of the present invention. The memory 136 can include, but is not limited to, the following types of devices: cache, ROM, PROM, EPROM, EEPROM, flash memory, SRAM, DRAM and magnetic disk. In some embodiments of the present invention, the memory 136 may be a content addressable memory (CAM).

As further illustrated in FIG. 1, the memory 136 may include several categories of software and data used in the data processing system 100: an operating system 152; application programs 154; input/output device drivers 158; and data 156. As will be appreciated by those of skill in the art, the operating system 152 may be any operating system suitable for use with a data processing system, such as OS/2, AIX or zOS from International Business Machines Corporation, Armonk, N.Y., Windows95, Windows98, Windows2000 or WindowsXP from Microsoft Corporation, Redmond, Wash., Unix or Linux. The input/output device drivers 158 typically include software routines accessed through the operating system 152 by the application programs 154 to communicate with devices such as the input/output circuits 146 and certain memory 136 components. The application programs 154 are illustrative of the programs that implement the various features of the circuits and modules according to some embodiments of the present invention. Finally, the data 156 represents the static and dynamic data used by the application programs 154, the operating system 152, the input/output device drivers 158, and other software programs that may reside in the memory 136. As illustrated in FIG. 1, the data 156 may include cohort files 130, 131 and 132, cohort member files 133 and 134 and reports 135 for use by the circuits and modules of the application programs 154 according to some embodiments of the present invention as discussed further herein.

Although three cohort files 130, 131 and 132, two cohort member files 133 and 134 and a single reports file 135 are illustrated in FIG. 1, embodiments of the present invention are not limited to this configuration. For example, more or less than three cohort files, more or less than two cohort member files and more than one reports file may be present without departing from the scope of the present invention. Furthermore, as further illustrated in FIG. 1, the cohort files 130, 131 and 132 may be present in one or more virtual file drawers. In other words, the same cohort files may be used in two different studies associated with two different file drawers. In particular, cohort file 1 is present in a first virtual file drawer 137 and cohort file 3 is present in a second virtual file drawer 138. Furthermore, cohort file 2 131 is present in the first and second virtual file drawers 137 and 138. Similarly, cohort member files may be present in one or more file drawers without departing from the scope of the present invention.

As further illustrated in FIG. 1, according to some embodiments of the present invention the application programs 154 include a project creation module 121, a query generation module 122, a search module 123, a report generation module 124, a cohort creation module 125, a storage module 126, a scheduling/delivery module 127 and a detail module 128. While the present invention is illustrated with reference to the project creation module 121, the query generation module 122, the search module 123, the report generation module 124, the cohort creation module 125, the storage module 126, the scheduling/delivery module 127 and the detail module 128 being application programs in FIG. 1, as will be appreciated by those of skill in the art, other configurations fall within the scope of the present invention. For example, rather than being application programs 154, these circuits and modules may also be incorporated into the operating system 152 or other such logical division of the data processing system 100. Furthermore, while the project creation module 121, the query generation module 122, the search module 123, the report generation module 124, the cohort creation module 125, the storage module 126, the scheduling/delivery module 127 and the detail module 128 are illustrated in a single data processing system, as will be appreciated by those of skill in the art, such functionality may be distributed across one or more data processing systems. Thus, the present invention should not be construed as limited to the configuration illustrated in FIG. 1, but may be provided by other arrangements and/or divisions of functions between data processing systems. For example, although FIG. 1 is illustrated as having various circuits and modules, one or more of these circuits or modules may be combined without departing from the scope of the present invention.

Figure 2:
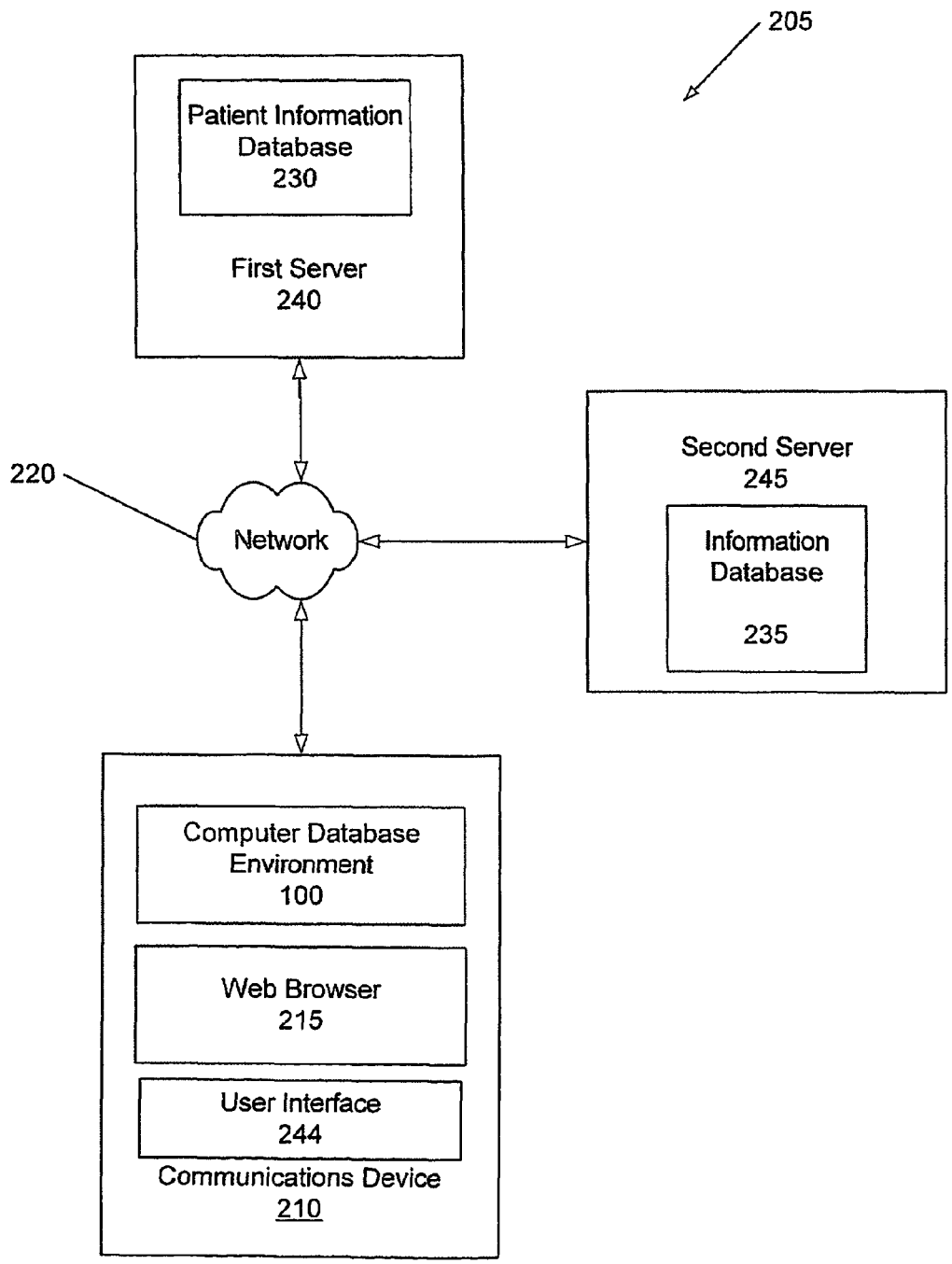
FIG. 2 is a block diagram illustrating some embodiments of the present invention in an exemplary network environment.

FIG. 2 illustrates an exemplary environment 205 for operations and devices according to some embodiments of the present invention. As illustrated in FIG. 2, the environment 205 may include a communications device 210, a network 220, a first server 240 and a second server 245. It will be understood that the communications device 210 illustrated in FIG. 2 may include the data processing system 100 or database environment discussed above with respect to FIG. 1. The communications device 210 may be, for example, a laptop computer, a desktop computer, a personal data assistant (PDA), a web capable mobile terminal or any device capable of communicating with the network 220. The communications device 210 may include a user interface 244 and a web browser 215 that may be accessed through the user interface 244. The first and second servers 240 and 245 may include first and second database environments 230 and 235, respectively, which may include patient records and information for use in some embodiments of the present invention. The communications device 210 may communicate over the network 220, for example, the internet, through a telephone line, a digital subscriber link (DSL), a broadband cable link, a wireless link or the like. The first and second servers 240 and 245 may also communicate over the network 220. Thus, the network 220 may convey data between the communications device 210 and the first and second servers 240 and 245.

Exemplary operations of methods, systems and computer program products according to some embodiments of the present invention will now be discussed with respect to FIGS. 1 and 2. When an owner (or administrator) of a research study begins a new study he or she may create a new virtual file drawer for the research study according to some embodiments of the present invention. The user interface 244 for the computer database environment 100 may be used to enter/provide project information associated with the research study or project. Before this information can be entered, in some embodiments of the present invention, a user may have to provide authorization information. In some embodiments of the present invention, the user may enter both user identification and a role code as discussed in, for example, copending U.S. patent application Ser. No. 11/349,408, filed Feb. 7, 2006, entitled METHODS, SYSTEMS AND COMPUTER PROGRAM PRODUCTS FOR PROVIDING A LEVEL OF ANONYMITY TO PATIENT RECORDS/INFORMATION, the disclosure of which is hereby incorporated herein by reference as if set forth in its entirety.

Once authorized, the user may enter cohort information, for example, demographic, genetic, clinical, and/or life style characteristics for the members of the cohort. As discussed above, as used herein, a "cohort" refers to a group or set of things or people sharing or potentially sharing one or more characteristics. For example, "characteristics" according to some embodiments of the present invention may include physical characteristics, presence or absence of a condition or conditions, age, geographic location and the like. The cohort may be defined by the person conducting the research study and a research study may include one or more cohorts. For example, a researcher may be researching the effect of a particular drug on breast cancer patients. Thus, the cohort may be defined by characteristics including female, breast cancer, from 25-35 years of age with either the BRCA1 or BRCA2 cancer-predisposing mutations.

In some embodiments of the present invention, the entered cohort information may be associated with an existing cohort. For example, existing cohorts may be split, merged and/or copied to provide the entered cohort information. Cohorts may be inherited from external systems and used as, for example reference cohorts.

Referring again to FIGS. 1 and 2, the user may also enter patient information, through the user interface 244, associated with members or possible members of the cohort associated with the research study. The patient information may include, for example, name, address, phone number, age, condition and details thereof and the like. The patient information may also include clinical data, such as test results, MRIs, xrays and the like associated with the patient. It will be understood that this information may be stored directly in the computer database environment or a link may be stored in the computer database environment 100 which allows access to information stored on external databases, for example, the patient information database 230 on the first server 240 and the information database 235 on the second server 240. Similar to cohorts, the entered patient information may be associated with an existing patient. For example, existing patient information may be split, merged, copied and/or inherited from external systems without departing from the scope of the present invention.

It will be understood that a project or research study may have from zero to N cohorts. A cohort may have from zero to M members (subjects, patients, and the like). A single cohort may belong to one or more research studies. Cohorts have roles or purposes, for example, a control cohort in research studies (projects) that may change over time. Cohort members also have roles or purposes, for example, control, rejected, drug, treatment, dropped and the like, in cohorts that may change over time.

Once the cohort/patient information is entered through the user interface 244, the project creation module 121 may be configured to generate a virtual project drawer associated with the research study or project to be stored in the computer database environment 100. The cohort information and/or patient information entered by the user may be placed in cohort files and the cohort files may include cohort member files including the patient information entered by the user. These files may all be stored in the virtual file drawer created for the project or research study. Once these files are created and stored they may be modified, searched, reorganized, deactivated and the like without departing from the scope of the present invention. Any manipulation of the data stored in the virtual file drawer, for example, addition, deletion, relocation, reorganization and the like, may be tracked, recorded and can be recreated at any point in the study according to some embodiments of the present invention.

The project creation module 121 may be configured to use a series of medical record numbers (MRNs), of patients entered by the user. A business intelligence tool may be used to create a query to return patients for a cohort. The project creation module 121 may be configured to prompt a user to upload a properly formatted document with patient MRNs or agreed upon unique identifier. In certain embodiments, the project creation module 121 may be configured to use an algorithm to create a statistically equivalent cohort based on selected criteria. Furthermore, the project creation module 121 may be configured merge existing cohorts or split existing cohorts to create a new cohort.

Thus, according to some embodiments of the present invention, preparing a report of the research study may be relatively less difficult as all of the information is stored and accessible electronically. For example, even information associated with rejected cohort members may be stored in the virtual file drawer with a role-rejected and the reasons therefore. Thus, the possibility of being accused of "cherry picking" cohort members may be reduced. Furthermore, building a statistically balanced cohort as discussed above may be relatively less difficult according to some embodiments of the present invention, which will be discussed further below.

In particular, a statistically balanced cohort can be generated using equations according to some embodiments of the present invention. To minimize the sum of the weights for the set of the study/control pairing, the following equation is used:

$$\text{Minimize: } \sum_{i=1}^{n} \sum_{j=1}^{m} \text{Weight}_{i,j} * SOS_{i,j} \quad \text{Equation (1) Objective Function}$$

Where n is the patient number in the treatment cohort and m is the patient number in the (statistically balanced) control cohort $$\text{Subject to: } \sum_{i=1}^{n} SOS_{i,j} = 1 \text{ For } j = 1, m \quad \text{Equation (2)}$$

In some embodiments of the present invention, each patient in the treatment cohort must be matched to exactly one patient in the control group (statistically balanced cohort), $$\sum_{j=1}^{m} SOS_{i,j} \le 1 = 1 \text{ For } i = 1, n \quad \text{Equations (3)}$$

Patients in the control group can be used zero or one times.

$$SOS_{i,j} \epsilon 0,1. \quad \text{Equation (4)}$$

The values of the selections vector can only take on the integer values of one or zero. Using equations to locate members of the statistically balanced cohort may allow these cohorts to be created relatively easier than if done without a computer database environment according to some embodiments of the present invention.

Although virtual file drawers discussed herein include cohort files and cohort member files, embodiments of the present invention are not limited by these examples. The virtual file folders may include any information associated with the project or research study. For example, a research grant application that preceded the beginning of the study may also be stored in the virtual file drawer without departing from the scope of the present invention. Furthermore, the project information may further include owner information, authorized user information, a title of the project and/or start and/or end dates associated with the project.

It will be understood that although the creation of a single virtual file drawer is discussed herein, embodiments of the present invention are not limited to this configuration. For example, two or more virtual file drawers 137 and 138 may be present in the computer database environment 100 without departing from the scope of the present invention. Furthermore, cohort files and/or cohort member files may be included in one or more virtual file drawers without departing from the scope of the present invention.

Once the cohort files and member files are created, a query generation module 122 may be configured to generate a query so as to locate project information, cohort information and/or patient information associated with the one or more of the projects (research studies) having associated virtual file drawers 137 and 138 in the computer database environment 100. The query generation module 122 may allow the user to generate a query by selecting data elements (columns) for report. For example, the user may select age, gender, stage total/positive nodes and the like. Also included may be predefined aggregation and data functions, for example, average age. The query generation module 122 may also be configured to allow the user to select pre-existing query filter elements (criteria). For example, the user may select a diagnosis data range, cancer type, grade, stage, patient demographics, provider and the like. The query generation module 122 may also be configured to allow a user to create any custom query filter elements. For example, a user may drag and drop elements needed for custom filter onto the query. Each of these data elements may be individually and collectively filtered. For example, "(provider in (Dr. A, Dr. B, Dr. C) or (age >65)) and (Gender=M)." The query generation module 122 may also be configured to allow the user to enter any Free Text/Semantic OmniFind criteria. For example, the user enters a Free Text or a Semantic Search.

In particular, the free text and semantic search tool Onmi-Find can be called to return results based on a users entered criteria when necessary. The free text and semantic criteria may be provided to OmniFind, which will execute the query. The results of the query may be provided to the computer database environment where they may be manipulated into a single report filter. The computer database environment may then insert that report filter into the user's report. At this point, control of the querying process may be returned to the query generation module 122 where the remaining elements of the querying may be handled. In some embodiments of the present invention, the query generation module 122 may be configured to build and manipulate the query, the data and input process in a business intelligence tool.

Once the query is generated, the search module 123 may be configured to search the virtual project drawers 137 and 138 according to the generated query so as to locate results therein that may be relevant to the research study. In some embodiments of the present invention, the search module 123 may be configured to use OmniFind. The report generation module 124 may be configured to generate a report including the located results.

In particular, once the search is complete, the report generation module 124 may be configured to generate the report responsive to a user selecting a "report" button on the user interface 244. In some embodiments of the present invention, the user may apply style/formatting template to the query result and may add any desired custom aggregations by inserting cells and defining aggregation, for example, average (LOS). The user may select sort criteria for the report by, for example, clicking on one or more columns of the report.

In other words, the query generation module 122 is further configured to modify the generated query. The search module 123 may be further configured to search the project drawers according to the modified query so as to locate modified results therein that may be relevant to the research study. The report generation module 124 may be further configured to generate a modified report including the modified results. As discussed above, the report generation module 124 is further configured to modify and/or customize the generated report based on user input.

Finalized reports may be stored, for example, in the reports 135 section of the memory 136. To access these reports, the user may be presented with a list of existing reports. A user may, for example, click on a desired report on a graphical user interface provided on the communications device 210. The graphical user interface according to some embodiments of the present invention may be customized to look like a researchers notebook, windows file system, and the like. In other words, the user can customize the interface so that it is familiar to them.

The report may be executed, modified or customized. The authorization level of the user accessing the report may define how a user is allowed to use the report. Depending on the roles/permissions, the user can execute, modify existing or customize existing reports. Customizing may allow for new reports to be built on existing ones without affecting the original.

According to some embodiments of the present invention, a finalized report stored in the memory 136 can be, for example, used to build a cohort, saved, scheduled, delivered and/or drilled down into. In particular, the cohort creation module 125 may be configured to build a cohort file based on the generated report. The cohort creation module 125 may be configured to communicate with the BI Tool to create a cohort from the generated report. The process may be instantiated when a user decides to create a cohort based of the results of an ad-hoc or structured report from the BI Tool. The cohort creation module 125 may be configured to save the BI Tool object and link to it from a cohort database record. The cohort, when modified at a later point, may use the BI Tool for modification. In some embodiments of the present invention, a user can run a query to view joiners i.e. patients that currently meet the query criteria used to define the cohort, but did not meet these criteria when the query was run last. This is accomplished by re-generating the report, but may only display those patients who joined since the previous run.

In some embodiments of the present invention, the storage module 126 may be configured to store the generated report. When the report is saved access levels may be set that define who can access the report, for example, what users with what roles. In certain embodiments of the present invention, the scheduling/delivery module 127 may be configured to schedule the generated report for a run. The run may be executed (the report may be executed) at the present moment or be delayed for later time. Furthermore, the delivery module 128 may be configured to determine a delivery method for the generated report.

Finally, in some embodiments of the present invention, the detail module 128 may be configured to drill down into the generated report to reveal underlying detail thereof. For example, if a column of the report indicates patient count, a user can, for example, click on the number of patients to reveal more detailed information about each of the patients, such as name, gender, age and test results.

Figure 3:
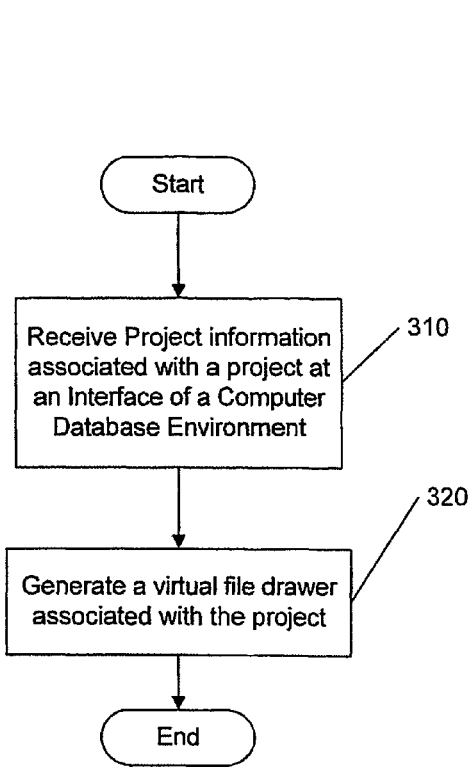
FIGS. 3, 4 and 5 are flowcharts illustrating operations according to various embodiments of the present invention.
Figure 4:
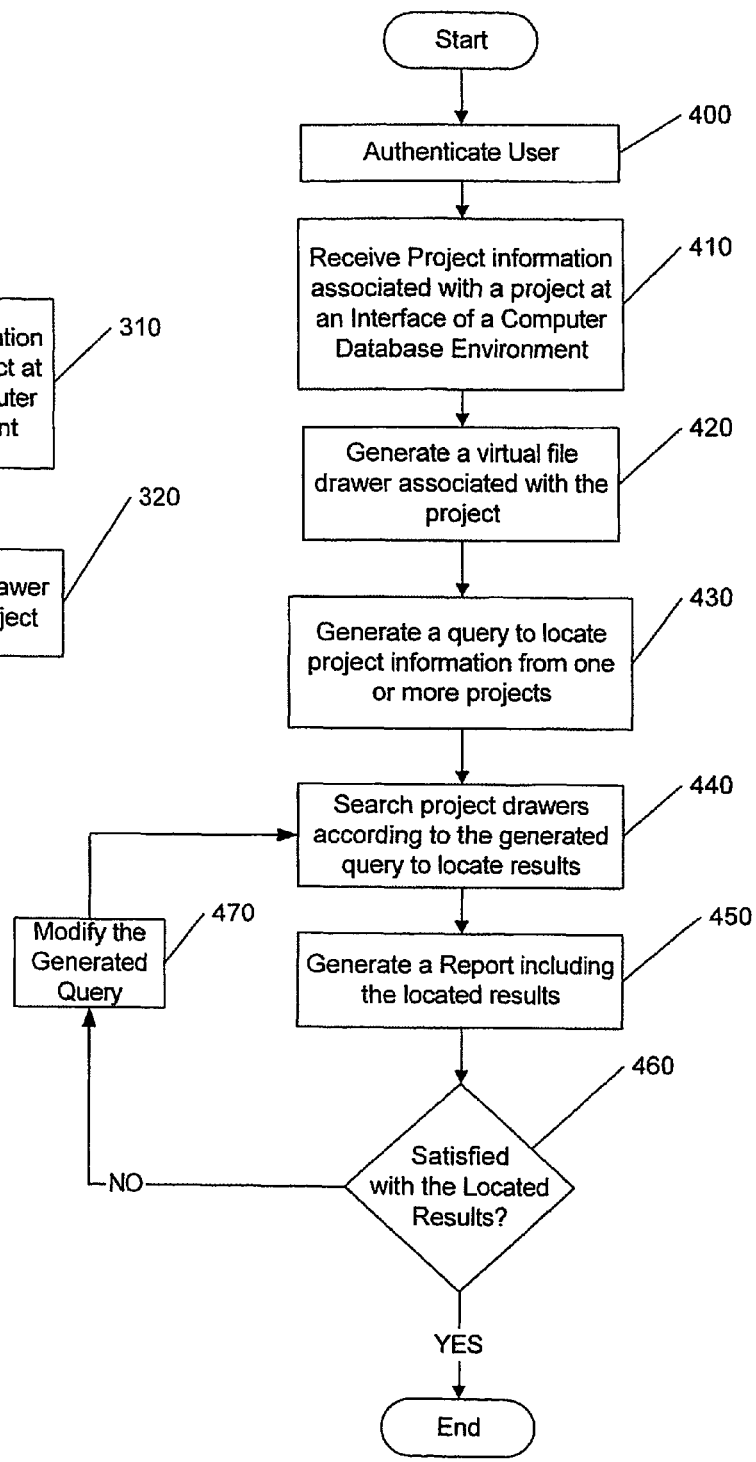
Figure 5:
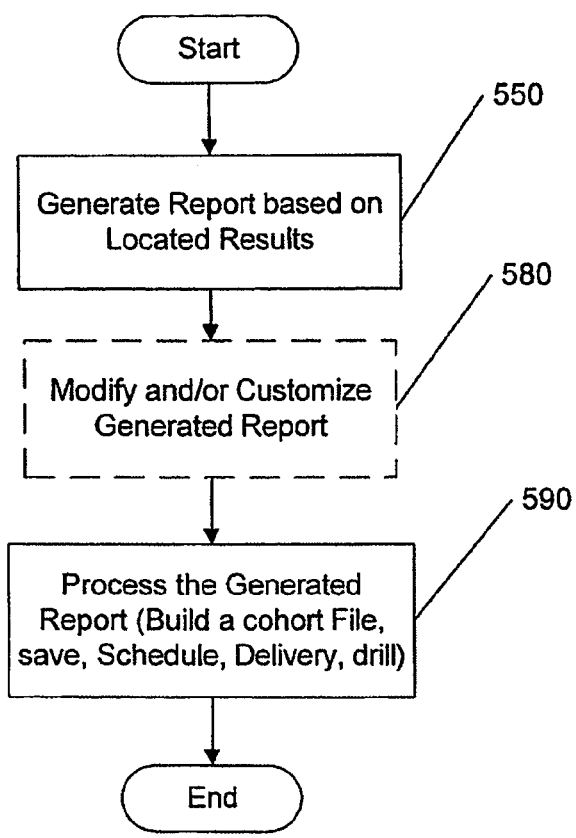

Operations for storing, organizing and/or manipulating cohort based information associated with a research study according to some embodiments of the present invention will now be discussed with respect to FIGS. 3 through 5. Referring now to FIG. 3, operations begin at block 310 by receiving project information associated with a first project at an interface of a computer database environment. The project information associated with the first project includes cohort information associated with one or more cohorts of the first project and patient information associated with members of the one or more cohorts of the first project. A first virtual project drawer associated with the first project may be generated to be stored in the computer database environment (block 320). The first virtual project drawer includes project information associated with the first project, one or more cohort files and/or two or more cohort member files.

In some embodiments of the present invention, cohorts can belong to more than one project. Cohorts can be generated by, for example, splitting, copying and/or merging existing cohort files and/or member files. Project information, according to some embodiments of the present invention, may include cohort data, patient information, owner information, authorized user information, a title of the project and/or start and/or end dates associated with the project. Cohort members of the project share one or more characteristics that define the cohort associated with the project and each of the cohort members of the project have at least one role associated therewith. The role may include, for example, initial data capture, control, rejected, drug, treatment and/or dropped.

Referring now to the flowchart of FIG. 4, operations according to further embodiments of the present invention will be discussed. Operations begin at block 400 by authenticating a user before allowing the user access to the computer database environment. Project information associated with a project is received at an interface of a computer database environment (block 410). The project information associated with the project includes cohort information associated with one or more cohorts of the project and patient information associated with members of the one or more cohorts of the project. A virtual project drawer associated with the project may be generated to be stored in the computer database environment (block 420). The virtual project drawer includes project information associated with the project, one or more cohort files and/or two or more cohort member files.

A query may be generated so as to locate project information, cohort information and/or patient information associated with the first and/or second projects (block 430). One or more project drawers may be searched according to the generated query so as to locate results therein that may be relevant to the research study (block 440). A report may be generated including the located results (block 450). It may be determined if the user is satisfied with the located results in the report (block 460). If it is determined that the user is not satisfied (block 460), the user may modify/customize the query (block 470) and blocks 440 through 470 may be repeated until the user is satisfied with the results (block 460).

If, on the other hand, the user is satisfied with the results (block 460), operations with respect to query modification may be complete.

Referring now to the flowchart of FIG. 5, operations according to further embodiments of the present invention will be discussed. Blocks represented by dotted lines are optional. A report based on the located results may be generated (block 550). In some embodiments of the present invention, the generated report may be modified or customized (block 580). The generated report (or modified/customized report) may be processed (block 590). For example, the a cohort file may be built based on the generated report, the generated report may be saved, the generated report may be scheduled for a run, a delivery method for the generated report may be determined and/or the generated report may be drilled into to reveal underlying detail associated with the located results as discussed above.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims are, therefore, to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

That which is claimed is:

1. A computer-implemented method for storing, organizing and/or manipulating cohort based information associated with a research study, the method comprising:

a processor receiving project information associated with a first project at an interface of a computer database environment, the project information associated with the first project including cohort information associated with at least one cohort of the first project and patient information associated with members of the at least one cohort of the first project, wherein the patient information is one or more of: name, address, phone number, age, and condition clinical data;

generating a first virtual project drawer associated with the first project to be stored in the computer database environment, the first virtual project drawer including project information associated with the first project, at least one cohort file and/or at least two cohort member files, receiving project information associated with a second project at the interface of the computer database environment, the project information associated with the second project including cohort information associated with at least one cohort of the second project and patient information associated with members of the at least one cohort of the second project;

generating a second virtual project drawer associated with the second project to be stored in the computer database environment, the second virtual project drawer including the project information associated with the second project, at least one cohort file and/or at least two cohort member files;

generating a query to locate project information, one or more cohort information and patient information associated with one or more of the first and second projects;

searching one or more of the first and second project drawers according to the generated query so as to locate results therein that may be relevant to the research study; and generating a report including the located results, wherein the generated report provides project information, one or more cohort information and patient information associated with one or more of the first and second projects.

2. The method of claim 1, wherein generating further comprises generating a query so as to locate at least one member and/or possible member of a statistically balanced control cohort.

3. The method of claim 1, wherein generating a query so as to locate at least one member and/or possible member of a statistically balanced control cohort comprising generating the query using the following equations:

to minimize a sum of weights for a set of a control pairing, the following equation is used: i=1 n .times. j=1 m .times. Weight i, j*SOS i, j, where n is a patient number in a treatment cohort and m is a patient number in the statistically balanced control cohort, subject to i=1 n .times. SOS i, j=1 .times. .times. For .times. .times. j=1, m.

4. The method of claim 3, wherein each member of the treatment cohort is matched to exactly one member of the statistically balanced control cohort represented by the following equation: j=1 m .times. SOS i, j .1toreq. 1=1 .times. .times. For .times. .times. i=1, nand wherein members of the statistically balanced control cohort can be used zero or one times represented by the following equation: SOS.sub.i,j.epsilon.0,1.

5. The method of claim 1, further comprising:
modifying the generated query;
searching the first and/or second project drawers according to the modified query so as to locate modified results therein that may be relevant to the research study; and
generating a modified report including the modified results.

6. The method of claim 1, further comprising modifying and/or customizing the generated report.

7. The method of claim 1, further comprising:
building a cohort file based on the generated report;
saving the generated report;
scheduling the generated report for a run;
determining a delivery method for the generated report; and/or
drilling down into generated report to reveal underlying detail associated with the located results.

8. The method of claim 1, wherein the cohort of the first project and/or the cohort of the second project belong to both the first and second projects.

9. The method of claim 1, wherein generating the first virtual project drawer is preceded by splitting, copying and/or merging existing cohort files and/or member files to provide the cohort file and/or member files associated with the first project.

10. The method of claim 1, wherein the project information associated with the first project further includes owner information, authorized user information, a title of the first project and/or dates associated with the first project.

11. The method of claim 1, wherein the cohort members of the first project share one or more characteristics that define the cohort associated with the first project and wherein each of the cohort members of the first project have at least one role associated therewith.

12. The method of claim 11, wherein the at least one role comprises initial data capture, control, rejected, drug, treatment and/or dropped.

13. The method of claim 1, wherein the first virtual project drawer includes multiple cohort files that each include at least two cohort member files.

14. The method of claim 1, further comprising authenticating a current user at the interface of the computer database environment so as to reduce the possibility of access by unauthorized users.

15. The method of claim 1, wherein the research study is associated with a healthcare issue.

16. A system, comprising:
a processor;
a storage facility for storing, organizing and/or manipulating cohort based information associated with a research study, the storage facility having stored thereon a utility which executes on the processor to provide the functions of:
a user interface of a computer database environment configured to receive project information associated with a first project, the project information associated with the first project including cohort information associated with at least one cohort of the first project and patient information associated with members of the at least one cohort of the first project wherein the patient information is one or more of: name, address, phone number, age, and condition clinical data;
a project creation module configured to generate a first virtual project drawer associated with the first project to be stored in the computer database environment, the first virtual project drawer including the project information associated with the first project, at least one cohort file and/or at least two cohort member files,
receiving project information associated with a second project at the interface of the computer database environment, the project information associated with the second project including cohort information associated with at least one cohort of the second project and patient information associated with members of the at least one cohort of the second project;
generating a second virtual project drawer associated with the second project to be stored in the computer database environment, the second virtual project drawer including the project information associated with the second project, at least one cohort file and/or at least two cohort member files;
generating a query to locate project information, one or more cohort information and patient information associated with one or more of the first and second projects;
searching one or more of the first and second project drawers according to the generated query so as to locate results therein that may be relevant to the research study; and
generating a report including the located results, wherein the generated report provides project information, one or more cohort information and patient information associated with one or more of the first and second projects.

17. The system of claim 16, wherein the query generation module is further configured to generate a query so as to locate at least one member and/or possible member of a statistically balanced control cohort.

18. The system of claim 17, wherein the query generation module is further configured to generate the query so as to locate at least one member and/or possible member of a statistically balanced control cohort using the following equations:
to minimize a sum of weights for a set of a control pairing, the following equation is used: $\sum_{i=1}^{n} \sum_{j=1}^{m} \text{Weight}_{i,j} \cdot SOS_{i,j}$, where n is a patient number in a treatment cohort and m is a patient number in the statistically balanced control cohort, subject to $\sum_{i=1}^{n} SOS_{i,j} = 1$ for $j=1, \ldots, m$.

19. The system of claim 18, wherein each member of the treatment cohort is matched to exactly one member of the statistically balanced control cohort represented by the following equation: $\sum_{j=1}^{m} SOS_{i,j} \leq 1$ for $i=1, \ldots, n$ and wherein members of the statistically balanced control cohort can be used zero or one times represented by the following equation: $SOS_{i,j} \in {0,1}$.

20. The system of claim 16:
wherein the query generation module is further configured to modify the generated query;
wherein the search module is further configured to search first and/or second project drawers according to the modified query so as to locate modified results therein that may be relevant to the research study; and wherein the report generation module if further configured to generate a modified report including the modified results.

21. The system of claim 16, wherein the report generation module is further configured to modify and/or customize the generated report.

22. The system of claim 16, further comprising:
a cohort creation module configured to build a cohort file based on the generated report;
a storage module configured to save the generated report;
a scheduling module configured to schedule the generated report for a run;
a delivery module configured to determine a delivery method for the generated report; and/or
a detail module configured to drill down into generated report to reveal underlying detail associated with the located results.

23. The system of claim 16, wherein the cohort of the first project and/or the cohort of the second project belong to both the first and second projects.

24. The system of claim 16, wherein project generation module is further configured to split, copy and/or merge existing cohort files and/or member files to provide the cohort file and/or member files associated with the first project.

25. The system of claim 16, wherein the project information associated with the first project further includes owner information, authorized user information, a title of the first project and/or dates associated with the first project.

26. The system of claim 16, wherein the cohort members of the first project share one or more characteristics that define the cohort associated with the first project and wherein each of the cohort members of the first project have at least one role associated therewith.

27. The system of claim 26, wherein the at least one role comprise initial data capture, control, rejected, drug, treatment and/or dropped.

28. The system of claim 16, wherein the first virtual project drawer includes multiple cohort files that each include at least two cohort member files.

29. The system of claim 16, further comprising an authentication module configured to authenticate a current user at the interface of the computer database environment so as to reduce the possibility of access by unauthorized users.

30. The system of claim 16, wherein the research study is associated with a healthcare issue.

31. A computer program product residing on a computer usable storage medium, for storing, organizing and/or manipulating cohort based information associated with a research study, the computer program product comprising:

computer readable program code configured to receive project information associated with a first project at an interface of a computer database environment, the project information associated with the first project including cohort information associated with at least one cohort of the first project and patient information associated with members of the at least one cohort of the first project, wherein the patient information is one or more of: name, address, phone number, age, and condition clinical data;

computer readable program code configured to generate a first virtual project drawer associated with the first project to be stored in the computer database environment, the first virtual project drawer the project information associated with the first project, at least one cohort file and/or at least two cohort member files;

computer readable program code configured to receive project information associated with a second project at the interface of the computer database environment, the project information associated with the second project including cohort information associated with at least one cohort of the second project and patient information associated with members of the at least one cohort of the second project;

computer readable program code configured to generate a second virtual project drawer associated with the second project to be stored in the computer database environment, the second virtual project drawer including the project information associated with the second project, at least one cohort file and/or at least two cohort member files;

computer readable program code configured to generate a query to locate project information, one or more cohort information and patient information associated with one or more of the first and second projects;

computer readable program code configured to search one or more of the first and second project drawers according to the generated query so as to locate results therein that may be relevant to the research study; and computer readable program code configured to generate a report including the located results, wherein the generated report provides project information, one or more cohort information and patient information associated with one or more of the first and second projects.

32. The computer program product of claim 31, further comprising computer readable program code configured to generate a query so as to locate at least one member and/or possible member of a statistically balanced control cohort.

33. The computer program product method of claim 32, wherein the computer readable program code configured to generate a query so as to locate at least one member and/or possible member of a statistically balanced control cohort is further comprising computer readable program code configured to generate using the following equations:

to minimize a sum of weights for a set of a control pairing, the following equation is used: i=1 n .times. j=1 m .times. Weight i, j*SOS i, j, where n is a patient number in a treatment cohort and m is a patient number in the statistically balanced control cohort, subject to i=1 n .times. SOS i, j=1 .times. .times. For .times. .times. j=1, m.

34. The computer program product of claim 33, wherein each member of the treatment cohort is matched to exactly one member of the statistically balanced control cohort represented by the following equation: j=1 m .times. SOS i, j .1toreq. 1=1.times. .times. For .times. .times. i=1, nand wherein members of the statistically balanced control cohort can be used zero or one times represented by the following equation: SOS.sub.i,j.epsilon.0,1.

35. The computer program product of claim 31, further comprising:

computer readable program code configured to modify the generated query;

computer readable program code configured to search the first and/or second project drawers according to the modified query so as to locate modified results therein that may be relevant to the research study; and computer readable program code configured to generate a modified report including the modified results.

36. The computer program product of claim 31, further comprising computer readable program code configured to modify and/or customize the generated report.

37. The computer program product of claim 31, further comprising:

computer readable program code configured to build a cohort file based on the generated report;

computer readable program code configured to save the generated report;

computer readable program code configured to schedule the generated report for a run;

computer readable program code configured to determine a delivery method for the generated report; and/or computer readable program code configured to drill down into generated report to reveal underlying detail associated with the located results.

38. The computer program product of claim 31, wherein the cohort of the first project and/or the cohort of the second project belong to both the first and second projects.

39. The computer program product of claim 31, further comprising computer readable program code configured to split, copy and/or merge existing cohort files and/or member files to provide the cohort file and/or member files associated with the first project.

40. The computer program product of claim 31, wherein the project information associated with the first project further includes owner information, authorized user information, a title of the first project and/or dates associated with the first project.

41. The computer program product of claim 31, wherein the cohort members of the first project share one or more characteristics that define the cohort associated with the first project and wherein each of the cohort members of the first project have at least one role associated therewith.

42. The computer program product of claim 41, wherein the at least one role comprises initial data capture, control, rejected, drug, treatment and/or dropped.

43. The computer program product of claim 31, wherein the first virtual project drawer includes multiple cohort files that each include at least two cohort member files.

44. The computer program product of claim 31, further comprising computer readable program code configured to authenticate a current user at the interface of the computer database environment so as to reduce the possibility of access by unauthorized users.

45. The computer program product of claim 35, wherein the research study is associated with a healthcare issue.

* * * * *